United States Patent
Price et al.

(10) Patent No.: US 9,746,584 B2
(45) Date of Patent: Aug. 29, 2017

(54) OPTICAL COMPUTING DEVICES COMPRISING ROTATABLE BROADBAND ANGLE-SELECTIVE FILTERS

(71) Applicant: Halliburton Energy Services, Inc., Houston, TX (US)

(72) Inventors: James M. Price, Spring, TX (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/316,871

(22) PCT Filed: Apr. 15, 2015

(86) PCT No.: PCT/US2015/025869
§ 371 (c)(1),
(2) Date: Dec. 7, 2016

(87) PCT Pub. No.: WO2016/167758
PCT Pub. Date: Oct. 20, 2016

(65) Prior Publication Data
US 2017/0131430 A1 May 11, 2017

(51) Int. Cl.
*E21B 49/08* (2006.01)
*G01V 8/20* (2006.01)
*G01V 5/08* (2006.01)

(52) U.S. Cl.
CPC .............. *G01V 8/20* (2013.01); *E21B 49/08* (2013.01); *G01V 5/08* (2013.01)

(58) Field of Classification Search
CPC ............ E21B 49/08; G01V 5/08; G01V 8/20
See application file for complete search history.

(56) References Cited

U.S. PATENT DOCUMENTS

| 6,198,531 B1 | 3/2001 | Myrick et al. |
| 6,529,276 B1 | 3/2003 | Myrick |
| 7,123,844 B2 | 10/2006 | Myrick |
| 7,834,999 B2 | 11/2010 | Myrick et al. |

(Continued)

FOREIGN PATENT DOCUMENTS

| WO | 2013163298 A1 | 10/2013 |
| WO | 2015116153 A1 | 8/2015 |

(Continued)

OTHER PUBLICATIONS

ISR/WO dated Jan. 28, 2016 for related PCT Application No. PCT/US2015/025869 filed Apr. 15, 2015.

(Continued)

*Primary Examiner* — Mark R Gaworecki
(74) *Attorney, Agent, or Firm* — McDermott Will & Emery LLP (57) ABSTRACT

An optical computing device comprising a plurality of electromagnetic radiation sources, each at a unique angular displacement about an optical train and each at at least one unique electromagnetic radiation wavelength; an integrated computational element (ICE) located in the optical train before or after a sample located in the optical train to generate modified electromagnetic radiation in the optical train; a broadband angle-selective filter (BASF) located in the optical train that is rotatable about an axis to a plurality of unique orientations to transmit the electromagnetic radiation and/or the modified electromagnetic radiation in the optical train at a target incident angle corresponding to one of the plurality of electromagnetic radiation sources to generate angle selected-modified electromagnetic radiation (ASMR); and a detector to receive the ASMR and to generate an output signal corresponding to a characteristic of the sample.

23 Claims, 2 Drawing Sheets

(56) References Cited

U.S. PATENT DOCUMENTS

| | | |
|---|---|---|
| 7,911,605 B2 | 3/2011 | Myrick et al. |
| 7,920,258 B2 | 4/2011 | Myrick et al. |
| 8,049,881 B2 | 11/2011 | Myrick et al. |
| 8,519,325 B1 | 8/2013 | Lu et al. |
| 8,575,541 B1 | 11/2013 | Jamison et al. |
| 8,619,256 B1 | 12/2013 | Pelletier et al. |
| 2009/0073433 A1 | 3/2009 | Myrick et al. |
| 2009/0182693 A1 | 7/2009 | Fulton et al. |
| 2009/0219538 A1 | 9/2009 | Myrick et al. |
| 2009/0219539 A1 | 9/2009 | Myrick et al. |
| 2012/0236297 A1 | 9/2012 | Uematsu et al. |
| 2012/0320578 A1 | 12/2012 | Flaming et al. |
| 2013/0031964 A1 | 2/2013 | Tunheim et al. |
| 2013/0031970 A1 | 2/2013 | Freese et al. |
| 2013/0031971 A1 | 2/2013 | Freese et al. |
| 2013/0031972 A1 | 2/2013 | Freese et al. |
| 2013/0032333 A1 | 2/2013 | Freese et al. |
| 2013/0032334 A1 | 2/2013 | Freese et al. |
| 2013/0032338 A1 | 2/2013 | Kalia et al. |
| 2013/0032339 A1 | 2/2013 | Kalia et al. |
| 2013/0032340 A1 | 2/2013 | Freese et al. |
| 2013/0032344 A1 | 2/2013 | Freese et al. |
| 2013/0032345 A1 | 2/2013 | Freese et al. |
| 2013/0032545 A1 | 2/2013 | Freese et al. |
| 2013/0032736 A1 | 2/2013 | Tunheim et al. |
| 2013/0033701 A1 | 2/2013 | Tunheim et al. |
| 2013/0033702 A1 | 2/2013 | Tunheim et al. |
| 2013/0034842 A1 | 2/2013 | Tunheim et al. |
| 2013/0035262 A1 | 2/2013 | Freese et al. |
| 2013/0284894 A1 | 10/2013 | Freese et al. |
| 2013/0284895 A1 | 10/2013 | Freese et al. |
| 2013/0284896 A1 | 10/2013 | Freese et al. |
| 2013/0284897 A1 | 10/2013 | Freese et al. |
| 2013/0284898 A1 | 10/2013 | Freese et al. |
| 2013/0284899 A1 | 10/2013 | Freese et al. |
| 2013/0284900 A1 | 10/2013 | Freese et al. |
| 2013/0284901 A1 | 10/2013 | Freese et al. |
| 2013/0284904 A1 | 10/2013 | Freese et al. |
| 2013/0286398 A1 | 10/2013 | Freese et al. |
| 2013/0286399 A1 | 10/2013 | Freese et al. |
| 2013/0287061 A1 | 10/2013 | Freese et al. |
| 2013/0324819 A1 | 12/2013 | Colvin |
| 2014/0061449 A1 | 3/2014 | Tunheim et al. |
| 2014/0061513 A1 | 3/2014 | Tunheim et al. |
| 2014/0067268 A1 | 3/2014 | Tunheim et al. |
| 2014/0076549 A1 | 3/2014 | Pelletier et al. |
| 2014/0076550 A1 | 3/2014 | Pelletier et al. |
| 2014/0076551 A1 | 3/2014 | Pelletier et al. |
| 2014/0078499 A1 | 3/2014 | Tunheim et al. |
| 2014/0080172 A1 | 3/2014 | Tunheim et al. |
| 2014/0080223 A1 | 3/2014 | Tunheim et al. |
| 2014/0080224 A1 | 3/2014 | Tunheim et al. |
| 2014/0081594 A1 | 3/2014 | Tunheim et al. |
| 2014/0110105 A1 | 4/2014 | Jones et al. |
| 2014/0116120 A1 | 5/2014 | Seckar |
| 2014/0121970 A1 | 5/2014 | Ljungdahl |
| 2014/0166361 A1 | 6/2014 | Jamison et al. |
| 2014/0166871 A1 | 6/2014 | Jamison et al. |
| 2014/0172177 A1 | 6/2014 | Jamison et al. |
| 2014/0202689 A1 | 7/2014 | Walton et al. |
| 2014/0231071 A1 | 8/2014 | Walton et al. |
| 2015/0346084 A1 | 12/2015 | Russell et al. |
| 2016/0091478 A1 | 3/2016 | Pearl, Jr. et al. |

FOREIGN PATENT DOCUMENTS

| | | |
|---|---|---|
| WO | 2015163853 A1 | 10/2015 |
| WO | 2016167758 A1 | 10/2016 |

OTHER PUBLICATIONS

Shen et al., Optical Broadband Angular Selectivity, Science, Mar. 28, 2014, 343(6178) 1499-1501.

B. T. Sullivan and J. A. Dobrowolski, "Implementation of a numerical needle method for thin-film design," Appl. Opt. 35, 5484-5492 (1996).

J. A. Dobrowolski and R. A. Kemp, "Refinement of optical multilayer systems with different optimization procedures," Appl. Opt. 29, 2876-2893 (1990).

Siegel et al., "Common Organic Contaminants in Cement and Bentonite Used for Water and Monitoring Well Construction," Chesapeake Energy, Jul. 10, 2013.

Sukhoivanov et al., Physics and Practical Modeling, ISMN 978-3-642-02645-4, Chapter 1, Introduction to Photonic Crystals (2009).

OPTICAL COMPUTING DEVICES COMPRISING ROTATABLE BROADBAND ANGLE-SELECTIVE FILTERS

BACKGROUND

The embodiments herein generally relate to systems and methods of optical computing and, more specifically, to optical computing devices comprising rotatable broadband angle-selective filters.

Optical computing devices, also commonly referred to as opticoanalytical devices, may provide improved sensitivity and detection limits when integrated computational elements are used. Such integrated computational elements may provide a relatively low cost, rugged, and accurate system for monitoring petroleum quality for the purpose of optimizing decision making at a well site and efficient management of hydrocarbon production. In some applications, the integrated computational elements may be useful in improving detection limits when determining a particular characteristic of a sample, such as a substance, compound, or material present in a wellbore, or other technology fields including, but not limited to, the food and drug industry, industrial applications, mining industries, or any field where it may be advantageous to determine in real-time a characteristic of a substance, compound, or material.

Space limitations may impact the design of optical computing devices. For example, it may be desirable to reduce the footprint of an optoanalytical devices to allow it to be included in process equipment or downhole oil and gas exploration equipment where space is limited. In other cases, it may be desirable to measure more than one analyte or characteristic in a sample with optical computing devices, where there is insufficient space to place multiple optoanalytical devices. In either of these two cases, advantages can be obtained from optical computing devices by reducing their footprint and combining multiple instruments into one housing.

Space saving techniques exist for traditional optical devices such as combining optical transducers into one housing to allow, for example, a camera to work in two distinct wavelength regions (e.g. Si detector for the UV-Vis and InGaAs detector for the NIR). For optical computing devices, space-saving techniques can also include combining multiple light sources into one housing, while sharing other optical components in the optical train (such as ICE core and detector) in a single optical computing system. However, traditional means of combining two or more optical components often require design considerations and/or beam steering optical components that can decrease the available light flux into an optical train (i.e. beam splitters).

BRIEF DESCRIPTION OF THE DRAWINGS

The following figures are included to illustrate certain aspects of the exemplary embodiments described herein, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The embodiments herein generally relate to systems and methods of optical computing and, more specifically, to optical computing devices comprising rotatable broadband angle-selective filters.

The exemplary systems and methods described herein employ various configurations of optical computing devices, also commonly referred to as "opticoanalytical devices," employing rotatable broadband angle-selective filters ("BASF") for the rapid analysis of a characteristic of a sample of interest, such as a sample in a flow path, a static sample, a sample on a conveyor belt, and the like. The disclosed systems and methods may be suitable for use in the oil and gas industry since the described optical computing devices provide a cost-effective, rugged, and accurate means for identifying one or more characteristics of a sample of interest in order to facilitate oil and gas production and/or safety of oil and gas wells. For example, the optical computing devices described herein may identify a characteristic of a sample in a flow path, such as a wellbore. Such characteristics may allow monitoring of petroleum quality for the purpose of optimizing decision making at a well site and efficient management of hydrocarbon production. It will be appreciated, however, that the various disclosed systems and methods are equally applicable to other technology fields including, but not limited to, the food and drug industry, industrial applications, mining industries, or any field where it may be advantageous to determine in real-time or near real-time a characteristic of a sample of interest, including flowing samples. As used herein, the term "flowing" refers to circulation or movement of a fluid sample with reference to the optical computing devices disclosed herein.

One or more illustrative embodiments incorporating the disclosure herein are presented below. Not all features of an actual implementation are described or shown in this application for the sake of clarity. It is to be understood that in the development of an actual embodiment incorporating the present disclosure, numerous implementation-specific decisions must be made to achieve the developer's goals, such as compliance with system-related, business-related, government-related and other constraints, which may vary by implementation and from time to time. While a developer's efforts might be complex and time-consuming, such efforts would be, nevertheless, a routine undertaking for one having ordinary skill in the art and the benefit of this disclosure.

It should be noted that when "about" is provided herein at the beginning of a numerical list, the term modifies each number of the numerical list. In some numerical listings of ranges, some lower limits listed may be greater than some upper limits listed. One skilled in the art will recognize that the selected subset will require the selection of an upper limit in excess of the selected lower limit. Unless otherwise indicated, all numbers expressing quantities of ingredients in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the exemplary embodiments described herein. At the very least, and not as an attempt to limit the application of the doctrine of equivalents to the scope of the claim, each numerical parameter should at least be construed in light of the number of reported significant digits and by applying ordinary rounding techniques.

While compositions and methods are described herein in terms of "comprising" various components or steps, the compositions and methods can also "consist essentially of" or "consist of" the various components and steps. When "comprising" is used in a claim, it is open-ended.

As used herein, the term "fluid" refers to any substance that is capable of flowing, including particulate solids, liquids, gases, slurries, emulsions, powders, muds, glasses, combinations thereof, and the like. In some embodiments, the fluid can be an aqueous fluid, including water or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid or a formation fluid. Fluids can include various flowable mixtures of solids, liquid and/or gases. Illustrative gases that can be considered fluids according to the present embodiments include, for example, air, nitrogen, carbon dioxide, argon, helium, hydrogen disulfide, mercaptan, thiophene, methane, ethane, butane, and other hydrocarbon gases, and/or the like.

As used herein, the term "characteristic" refers to a chemical or physical property of a substance. A characteristic of a substance may include a quantitative value of one or more chemical components therein. Such chemical components may be referred to as "analytes." Illustrative characteristics of a substance that can be monitored with the optical computing devices disclosed herein may include, for example, chemical composition (identity and concentration, in total or of individual components), impurity content, pH, viscosity, density, ionic strength, total dissolved solids, salt content, porosity, opacity, bacteria content, combinations thereof, and the like.

As used herein, the term "electromagnetic radiation" refers to infrared radiation, near-infrared radiation, visible light, ultraviolet light, vacuum ultraviolet light, X-ray radiation, gamma ray radiation, and any combination thereof.

As used herein, the term "optical computing device" refers to an optical device that is configured to receive an input of electromagnetic radiation from a substance or sample of the substance (collectively referred to as "sample") and produce an output of electromagnetic radiation from a processing element. The processing element may be, for example, an integrated computational element ("ICE"). The electromagnetic radiation emanating from the processing element is changed in some way so as to be readable by a detector, such that an output signal of the detector may be correlated to at least one characteristic of the sample. The output of electromagnetic radiation from the processing element can be reflected electromagnetic radiation, transmitted electromagnetic radiation, and/or dispersed electromagnetic radiation. As will be appreciated, whether reflected or transmitted electromagnetic radiation is analyzed by the detector will be a matter of routine experimental design. In addition, emission and/or scattering of the substance, for example via fluorescence, luminescence, radiating and re-radiating, Raman scattering, and/or Raleigh scattering can also be monitored by the optical computing devices.

As used herein, the term "sample," or variations thereof, refers to at least a portion of a substance of interest to be tested or otherwise evaluated using the optical computing devices described herein. The sample includes the characteristic of interest, as defined above, and may be any fluid, as defined herein, or otherwise any solid substance or material such as, but not limited to, rock formations, concrete, other solid surfaces, etc.

As used herein, the term "optically-interact" or variations thereof refers to the reflection, transmission, scattering, diffraction, radiating, re-radiating, or absorption of electromagnetic radiation either on, through, or from one or more processing elements, such as integrated computational elements. Accordingly, optically-interacted light refers to light that has been reflected, transmitted, scattered, diffracted, or absorbed by, emitted, radiated or re-radiated, for example, using the integrated computational elements, but may also apply to interaction with a sample substance.

Unlike conventional spectroscopic instruments, which measure and produce an electromagnetic spectrum of a sample needing further interpretation to obtain a result, the ultimate output of optical computing devices described herein is a real number that can be correlated in some manner with a characteristic of a sample of interest. As used herein, a "broadband angle-selective filter" (or "BASF") refers to a filter that screens broadband light with respect to an angle of incidence. As used herein, the term "angle of incidence" refers to the angle that an incident ray of electromagnetic radiation makes normal to a surface.

The use of the rotatable BASFs of the present disclosure in the optical computing devices may provide a number of additional advantages. For example, where a single characteristic of a sample is being evaluated (e.g., an analyte of the sample), the rotatable BASF may allow high optical transmission of electromagnetic radiation at a particular angle of incidence from a particular electromagnetic radiation source, even when multiple electromagnetic radiation sources are directed at the BASF. Accordingly, although multiple discontinuous wavelengths from multiple electromagnetic radiation sources are directed in an optical train of the optical computing device, the rotatable BASF can be positioned at a unique angular orientation to accept only those wavelengths from the desired electromagnetic radiation source at a particular angle of incidence. Accordingly, the rotatable BASF of the present disclosure provides such an advantage over traditional filter photometer or dispersive spectroscopic based systems that have multiple wavelength selection devices with low optical throughput at each wavelength.

Another advantage of the optical computing devices employing the rotatable BASFs of the present disclosure is that it can easily be employed to measure multiple characteristics (e.g., analytes) of a sample. For example, where an ICE is used in the optical computing device, the ICE may be configured to operate in a certain range of wavelengths associated with multiple characteristics of a sample to be evaluated. The rotatable BASF can thus be rotated to allow transmission of a particular wavelength of electromagnetic radiation from a particular electromagnetic radiation source based on its angle of incidence, and can thereafter be rotated to a second orientation to allow transmission of a different wavelength of electromagnetic radiation from a different electromagnetic radiation source based on its angle of incidence, and so on. Each wavelength permitted into the optical train is thus appropriate for the particular characteristics of the sample being evaluated. Thus, the optical computing devices of the present disclosure comprising the rotatable BASFs simplify previously used optical computing devices by removing the need for multiple-filter wheels, which may be large in size, containing multiple ICE cores that each operate at a different wavelength associated with different characteristics of interest of a sample.

The embodiments herein including optical computing devices comprising rotatable BASFs described herein accordingly allow integration of multiple electromagnetic radiation sources (e.g., having different operational wavelengths) into a single optical computing device, permit high optical throughput (e.g., high signal-to-noise ratios) that operate in multiple discontinuous wavelength regions with a single moving part (e.g., the rotatable BASF, which as discussed in detail below, may also form a multi-layer film stack on a component of the optical computing device), remove the need for multiple-filter wheels having multiple ICEs for analyzing multiple characteristics of one or more samples, simplify optical arrangement of optical computing devices in terms of equipment size and footprint, significantly improve system performance sensitivity when used in reflection modes, and the like.

In addition, significant benefits may be realized by combining the outputs from two or more integrated computational elements and/or two or more rotatable BASFs within an optical computing device with one another, when analyzing a sample. Specifically, in some instances, significantly increased detection accuracy may be realized. Any of the methods described herein may be carried out by combining the outputs of two or more integrated computational elements and/or two or more rotatable BASFs with one another. The integrated computational elements and/or rotatable BASFs whose outputs are being combined may be associated or disassociated with a characteristic of interest, display a positive or negative response when analyzing the characteristic of interest, or any combination thereof.

As alluded to above, the operational simplicity of optical computing devices makes them rugged and well suited for field or process environments, including deployment within a subterranean formation. For example, the optical computing devices described herein may analyze fluids commonly encountered in the oil and gas industry, including while deployed within a subterranean formation.

A significant and distinct advantage of the optical computing devices disclosed herein is that they can be configured to specifically detect and/or measure a characteristic of a sample, thereby allowing qualitative and/or quantitative analyses of the characteristic without having to undertake a time-consuming sample processing procedure, with or without having to record and process the sample's electromagnetic spectrum. With rapid analyses capabilities on hand, the exemplary systems and methods described herein may be able to determine the percentage of a characteristic of a sample so that an operator may determine whether the characteristic is within a particular acceptable limit range. If the characteristic of the sample is outside of the acceptable limit range (typically too high), then corrective measures may be taken. The use of the optical computational devices described herein to detect a characteristic of a sample may further be beneficial to allow for the collection and archival of information relating to such samples for particular operations, in conjunction with operational information, to optimize subsequent operations, and the like.

In some embodiments, the present disclosure provides an optical computing device comprising an electromagnetic radiation source that emits electromagnetic radiation into an optical train. As used herein, the term "optical train" refers to the path that electromagnetic radiation traverses originating at a source and terminating at a detector. Within the optical train, a sample, an integrated computational element ("ICE"), and a BASF are positioned in any configuration. That is, the sample may come before or after the ICE, the ICE may come before or after the BASF, and the BASF may come before or after the sample. Moreover, more than one ICE and/or more than one BASF may be in the optical train, without departing from the scope of the present disclosure.

The exemplary systems and methods described herein include at least one optical computing device configured to measure at least one characteristic of a sample, such as in a flow path which may be in a subterranean formation (e.g., a wellbore). In some embodiments, the optical computing devices suitable for use in the exemplary systems and methods described herein may be mobile or portable.

In accordance with the embodiments described herein, an optical computing device may include an electromagnetic radiation source, at least one processing element (e.g., an ICE), at least one rotatable BASF, and at least one detector arranged to receive optically interacted light after it has interacted with the at least one ICE, the at least one BASF, and a sample, in any combination. In some embodiments, the exemplary optical computing devices may be specifically configured for detecting, analyzing, and quantitatively measuring a particular characteristic of a sample, such as a concentration of a component of the sample or other characteristics discussed in greater detail below. In other embodiments, the optical computing devices may be general purpose optical devices, with post-acquisition processing (e.g., through computer means) being used to specifically detect the characteristic of the sample.

The presently described optical computing devices combine the advantage of the power, precision, and accuracy associated with laboratory spectrometers, while being extremely rugged and suitable for field use. Furthermore, the optical computing devices can perform calculations (analyses) in real-time or near real-time without the need for time-consuming sample processing. In this regard, the optical computing devices can be specifically configured to detect and analyze particular characteristics of a sample. In some embodiments, the detected output can be converted into a voltage that is distinctive of the magnitude of the characteristic of the sample.

The optical computing devices of the present disclosure operate by discriminating between optical (or voltage) signals related to a characteristic of a sample and interfering signals (e.g., stray light or "ghost" signals). Such stray light (also referred to as "stray light reflections" herein) relates to an optical signal that is not related to the sample of interest, and that may have a tendency to vary the desired signal conveyed through the optical train and corresponding to the sample or characteristic thereof. In some embodiments, the stray light may be related to characteristics of a sample that are not of interest or, in some instances, may be related to radiating deviations including, for example, intensity fluctuations in the electromagnetic radiation, interferent fluctuations (e.g., dust or other interferents passing in front of an electromagnetic radiation source), coatings on windows included with the optical computing device (e.g., sampling windows), combinations thereof, or the like.

If not effectively reduced or otherwise prevented, the stray light may serve to adversely vary the detected electromagnetic radiation, resulting in substantially reduced accuracy, precision, sensitivity, and limit of detection. Previous means of reducing stray light relied on physical masking techniques, apertures, and shields, for example. However, in addition to the benefits described previously with regard to the rotatable BASFs of the present disclosure, the rotatable BASFs in combination with the ICE components in the optical computing devices described herein also reduce or eliminate stray light and increase the sensitivity and output signal of the optical computing devices comprising them (e.g., reduce the signal-to-noise ratio), as compared to previously used means.

The optical computing devices can be configured to detect not only the composition and concentrations of a sample, but they can also be configured to determine physical properties and other characteristics of the sample as well, based on their analysis of the electromagnetic radiation received from the optical train comprising the sample. For example, the optical computing devices can be configured to determine the concentration of the sample and correlate the determined concentration to a characteristic of the sample by using suitable processing means. As will be appreciated, the optical computing devices may be configured to detect as many characteristics as desired for a given sample. All that is required to accomplish the monitoring of multiple characteristics of interest is the incorporation of suitable processing and detection means within the optical computing device for each characteristic of interest (e.g., concentration of an analyte, and the like). In some embodiments, the properties of the sample may be determined using a combination of characteristics of interest (e.g., a linear, non-linear, logarithmic, and/or exponential combination). Accordingly, the more characteristics that are detected and analyzed using the optical computing devices, the more accurately the properties of the sample will be determined. For example, properties of a sample that may be determined using optical computing devices described herein may include, but are not limited to, the absolute concentration of an analyte, the relative ratios of two or more analytes, the presence or absence of an analyte, and the like, and any combination thereof.

The optical computing devices described herein utilize electromagnetic radiation to perform calculations, as opposed to the hardwired circuits of conventional electronic processors. When electromagnetic radiation interacts with a sample, unique physical and chemical information about the sample may be encoded in the electromagnetic radiation that is reflected from, transmitted through, or radiated in an optical train comprising the sample. The optical computing devices described herein are capable of extracting the information of the spectral fingerprint of multiple characteristics of a sample, and converting that information into a detectable output regarding the overall properties of the monitored material of interest. That is, through suitable configurations of the optical computing devices, electromagnetic radiation associated with characteristics of interest can be separated from electromagnetic radiation associated with all other components of the material of interest in order to estimate the properties of the monitored substance (e.g., a contaminant) in real-time or near real-time, particularly by synergistic operation of the one or more ICEs and one or more rotatable BASFs comprising the optical computing devices.

Figure 1:
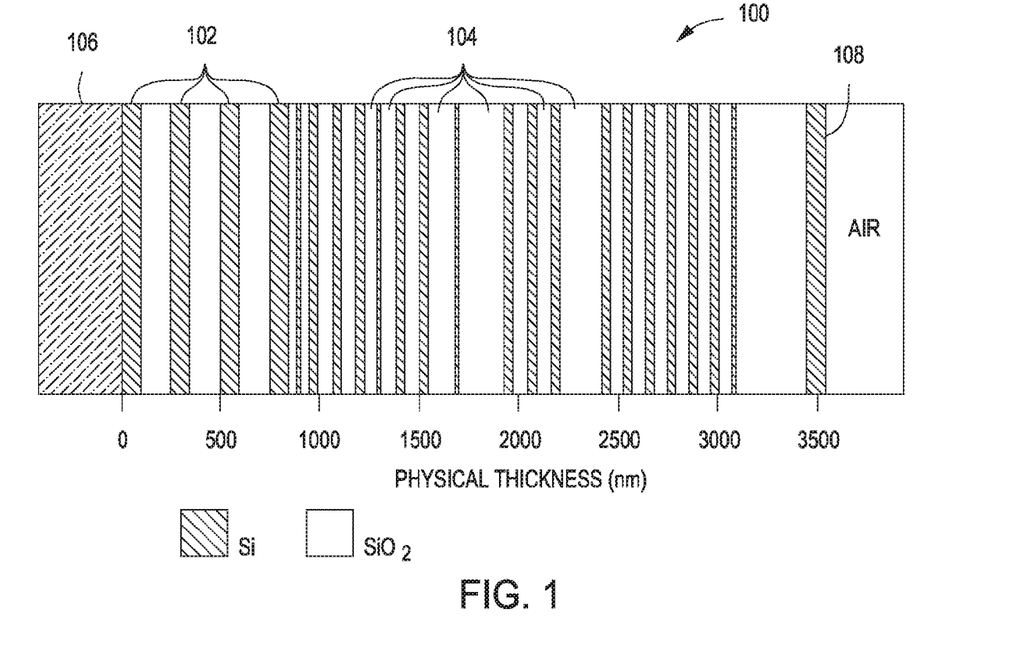
FIG. 1 illustrates an exemplary integrated computation element, according to one or more embodiments described herein.

The processing elements used in the exemplary optical computing devices described herein may be characterized as integrated computational elements (ICE). Each ICE is capable of distinguishing electromagnetic radiation that has optically interacted with a sample in an optical train from other electromagnetic radiation. Referring to FIG. 1, illustrated is an exemplary ICE 100 suitable for use in the optical computing devices used in the systems and methods described herein. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, $SiO_x$, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of interest using a conventional spectroscopic instrument. The spectrum of interest of a given characteristic of interest typically includes any number of different wavelengths. It should be understood that the exemplary ICE 100 in FIG. 1 does not in fact represent any particular characteristic of interest, but is provided for purposes of illustration only. Consequently, the number of layers 102, 104 and their relative thicknesses, as shown in FIG. 1, bear no correlation to any particular characteristic of interest. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the materials to the monitored substance.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 may contain a corresponding vessel (not shown), which houses the gases or liquids. Exemplary variations of the ICE 100 may also include holographic optical elements, gratings, piezoelectric, light pipe, digital light pipe (DLP), molecular factor devices, variable optical attenuators, and/or acousto-optic elements, for example, that can create transmission, reflection, and/or absorptive properties of a material of interest or contaminant.

The multiple layers 102, 104 exhibit different refractive indices. By properly selecting the materials of the layers 102, 104 and their relative thickness and spacing, the ICE 100 may be configured to selectively transmit/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic of interest. These methods may include inverse Fourier transform (IFT) of the optical transmission spectrum and structuring the ICE 100 as the physical representation of the IFT. The approximations convert the IFT into a structure based on known materials with constant refractive indices.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the integrated output light intensity of the ICE 100 is related to the characteristic of interest.

The rotatable BASF of the present disclosure may be used at any location in the optical train, described in more detail below, to transmit electromagnetic radiation at a target incident angle, thereby selectively permitting electromagnetic radiation from a particular electromagnetic radiation source to optically interact with a sample and enhancing the signal-to-noise ratio in the optical train relating to the sample or characteristic of interest of the sample that is received by a detector. When the signal has interacted with a sample, the refractive index of many types of samples may not be highly sensitive to wavelength, and thus the target incident angle may be the same for a broad band of frequencies using the same rotatable BASF. The rotatable BASF reflects all or substantially all electromagnetic radiation propagating at angles that are not coincident with the target incident angle. As used herein, the term "substantially" means largely, but not necessarily wholly.

Any BASF may be used in the optical train in accordance with the methods of the present disclosure, where the BASF is rotatable about an axis relative to a plurality of electromagnetic radiation sources in an optical train. In some embodiments, the ability of a BASF to transmit radiation signals at a target angle of incidence originating from a particular electromagnetic radiation source (e.g., from one or multiple electromagnetic radiation sources directed in an optical train) may depend largely on the existence of optical band gaps in the BASF that prevent light propagation at particular frequencies and transmit those at an incident angle, and the ability of photonic heterostructures to broaden such band gaps. As used herein, the term "band gap," and grammatically variants thereof, refers to ranges of photon frequencies where no photons can be transmitted through a material. As used herein, the term "photonic heterostructures" (or simply "heterostructures") refers to a stacking of photonic materials (e.g., photonic crystals) having different optical refractive indices. In some embodiments, the heterostructures described herein may be formed using quarter-wave stacks having varying refractive indices, each one quarter of an optical wavelength in thickness.

The "refractive index" of a material (e.g., a sample of interest) of an optical medium is a dimensionless number that describes how much electromagnetic radiation is bent, or refracted, as it propagates through a material. The refractive index (n) of a material is determined by Equation 1:

$$n = \sqrt{\epsilon_r \mu_r}$$

Equation 1, where $\epsilon_r$ is the material's relative permittivity, and $\mu_r$ is the material's relative permeability. A materials relative permittivity and relative permeability are frequency, and thus wavelength, dependent. Typically, for most naturally occurring materials, the relative permeability of a material is substantially equal to one (the integer 1) at optical frequencies (although not always) and, accordingly, the variable refractive indices of the photonic material (e.g., photonic crystal) in the heterostructures described herein may be based substantially, or wholly, on the material's relative permittivity.

Figure 2:
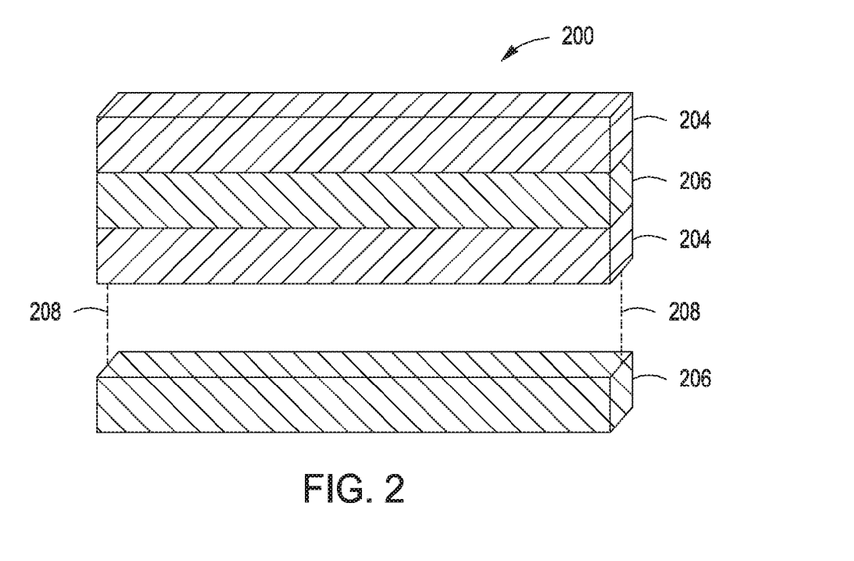
FIG. 2 illustrates a representative photonic heterostructure for use as a broadband angle-selective filter, according to one or more embodiments described herein.

Referring now to FIG. 2, illustrated is a representative photonic heterostructure 200 that may be used to form the rotatable BASFs of the present disclosure. The heterostructure 200 is formed from alternating layers of a high-index photonic material 204 and a low-index photonic material 206. As depicted by the dashed lines 208, the number of layers of high-index photonic material 204 and low-index photonic material 206 may vary depending on the design of the heterostructure 200. For example, the layers of the heterostructure 200 may comprise greater than about 5 bilayers, where a bilayer includes one high-index material 204 layer and one low-index material 206 layer. That is, the number of bilayers is not limited according to the methods of the present disclosure. In some embodiments, the number of bilayers in the quarter-wave stack 202 may be between a lower limit of about 5 bilayers, 10 bilayers, 20 bilayers, 30 bilayers, 40 bilayers, 50 bilayers, 60 bilayers, 70 bilayers, 80 bilayers, 90 bilayers, 100 bilayers, 110 bilayers, 120 bilayers, 130 bilayers, 140 bilayers, 150 bilayers, 160 bilayers, 170 bilayers, 180 bilayers, 190 bilayers, 200 bilayers, 210 bilayers, 220 bilayers, 230 bilayers, 240 bilayers, and 250 bilayers to an upper limit of about 500 bilayers, 490 bilayers, 480 bilayers, 470 bilayers, 460 bilayers, 450 bilayers, 440 bilayers, 430 bilayers, 420 bilayers, 410 bilayers, 400 bilayers, 390 bilayers, 380 bilayers, 370 bilayers, 360 bilayers, 350 bilayers, 340 bilayers, 330 bilayers, 320 bilayers, 310 bilayers, 300 bilayers, 290 bilayers, 280 bilayers, 270 bilayers, 260 bilayers, and 250 bilayers, encompassing any value and subset therebetween, even or odd. In some embodiments, each of the layers or bilayers may additionally comprise bilayers to further refine the band gaps desired for a particular BASF comprising the heterostructure 200.

As an increasing number of high-index photonic material 204 and low-index photonic material 206 bilayers are added, the transmission of certain incident angles of electromagnetic radiation decreases, thus increasing reflection of these incident angles. That is, the band gap is modified by altering the number of high-index photonic material 204 and low-index photonic material 206 bilayers. As depicted, the heterostructure 200 comprises alternating layers of high-index photonic material 204 and low-index photonic material 206 bilayers; however, in other embodiments, the heterostructure 200 may have photonic material layers (or bilayers, or layers comprising one or more bilayers) that represent a geometric series of refractive indices, such that the refractive indices of the layers increase or decrease geometrically, thereby also modifying the band gap for particular wavelengths of electromagnetic radiation.

As depicted, the heterostructure 200 includes 1:1 stacks (i.e., bilayers) having equal thickness, such as equal optical thickness (e.g., one quarter of an optical wavelength in thickness). However, higher-order stacking may also be suitable for use as the rotatable BASF of the present disclosure. For example, 2:1 or 3:1 stacking may be suitable of high-index photonic material 204:low-index photonic material 206, or of low-index photonic material 206:high-index photonic material 204. Other higher-order stacking may also be employed, without departing from the scope of the present disclosure. Moreover, the double or triple stacking of one type of photonic material may be effectively a single layer with an increased thickness. In these higher-order stacks, the ratio between the optical thickness of high-index photonic material and low-index photonic material may be adjusted in integer multiples, such as by reducing the thickness of the high-index photonic material while preserving the desired spectral band gaps.

In some embodiments, the size, thickness, or shape of two adjacent photonic materials in a heterostructure forming a rotatable BASF according to the present disclosure may be varied to achieve a desired band gap. For example (not shown), a second layer A may be arranged such that it is of a smaller size than a first and third layer B that surround layer A. The second layer A may have a photonic band gap that lies within the photonic band gap of the first and third layer B. Accordingly, electromagnetic radiation having a wavelength outside of the band gap of layer A but inside the band gap of layers B will be reflected by layers B and thus retained within layer A.

In some embodiments, the material forming the layers of the heterostructure 200 for forming the rotatable BASF may be any photonic crystal material including isotropic and anisotropic material, which may be alternated or otherwise arranged relative to each other in the layers forming the heterostructure 200. The photonic crystal layers may include, but are not limited to, a silicon-based compound (e.g., silicon dioxide, silicon, and the like), a tantalum-based compound (e.g., tantalum pentoxide, and the like), a Group III-V semiconductor compound (e.g., gallium arsenide, indium gallium arsenide, indium phosphide, and the like), a Group IVB metal compound (e.g., titanium oxide, zirconium oxide, hafnium oxide, and the like), a dielectric, and any combination thereof.

Figure 3:
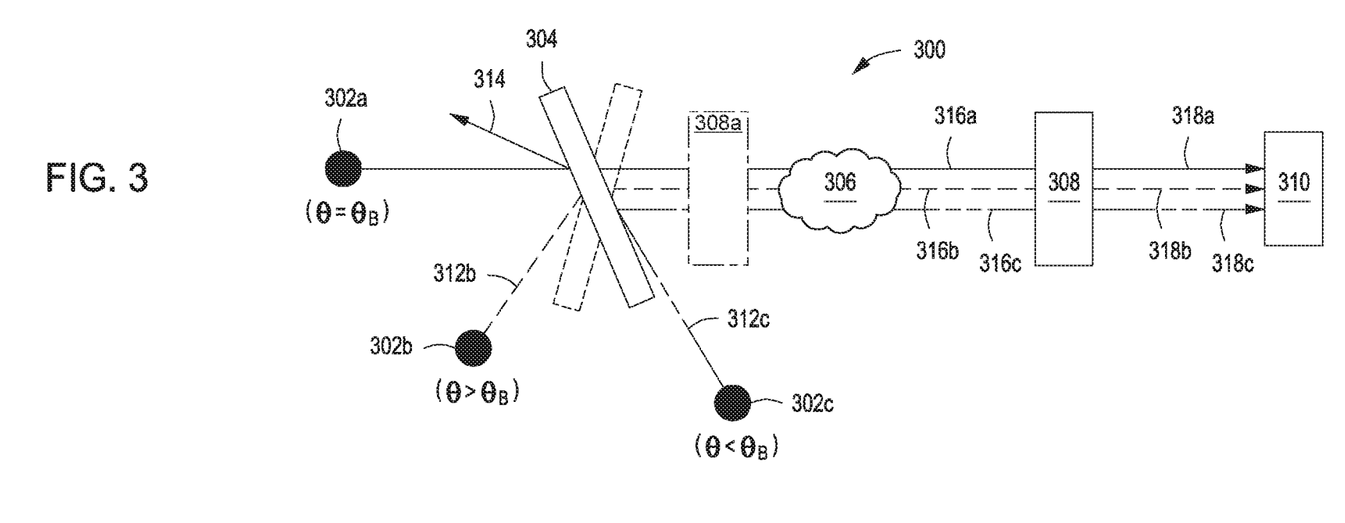
FIG. 3 illustrates an optical computing device comprising a rotatable broadband angle-selective filter, according to one or more embodiments described herein.

Referring now to FIG. 3, illustrated is a block diagram that non-mechanistically illustrates how an optical computing device 300 comprising a rotatable BASF and an ICE is able to distinguish electromagnetic radiation related to a characteristic of interest in a sample, according to one or more embodiments herein. The rotatable BASF is able to transmit electromagnetic radiation at a target angle of incidence coming from a particular electromagnetic radiation source, and reflect electromagnetic radiation that is not coincident with the target angle of incidence (e.g., that is not from the particular electromagnetic radiation source of interest). As shown in FIG. 3, the optical computing device comprises a plurality of electromagnetic radiation sources 302a, 302b, and 302c; a rotatable BASF 304, an ICE 308, and a detector 310. A sample 306 is located in the optical train created by each of the electromagnetic radiation sources 302a,b,c. While not shown, the device 300 may be housed within a casing or housing configured to substantially protect the internal components of the device 300 from damage or contamination from the external environment. The housing may operate to mechanically couple or otherwise place in communication the device 300 to a flow path (not shown) that comprises the sample 306 and places the sample in the optical train. The housing may mechanically couple the device 300 to a flow path with, for example, mechanical fasteners, brazing or welding techniques, adhesives, magnets, other fastening devices, combinations thereof, or the like.

Each electromagnetic radiation source 302a,b,c may be configured to emit or otherwise generate electromagnetic radiation, 312a, 312b, and 312c, respectively, and may be any device capable of so doing. For example, the electromagnetic radiation sources 302a,b,c may be a light bulb, a light emitting device (LED), a laser, a blackbody, a photonic crystal, an X-Ray source, a gamma ray source, combinations thereof, or the like. Each electromagnetic radiation source 302a,b,c may emit a different wavelength of electromagnetic radiation, such as to cover a wider range of wavelengths that may be selective for one or more particular samples or characteristics of samples. That is, each of the electromagnetic radiation sources 302a,b,c may emit a different wavelength or wavelength band. Where wavelength bands are selected, the wavelength bands may overlap at some wavelengths, without departing from the scope of the present disclosure. Accordingly, the electromagnetic radiation sources may emit single band, narrow band, or broadband wavelengths, and any combination thereof (each collectively referred to simply as "wavelength" herein).

Although the embodiment in FIG. 3 depicts three electromagnetic radiation sources, it will be appreciated that any number of electromagnetic radiation sources may be used in accordance with the embodiments of the present disclosure, including one, two, or greater than three, such as four, five, six, seven, eight, nine, ten, or even more, without departing from the scope of the present disclosure. The upper limit of electromagnetic radiation sources, in some embodiments, may be equal to n, where n is equal to the number of discrete wavelengths over which the one or more ICE in the optical train is designed to optically interact with. The number of electromagnetic radiation sources may be selected dependent on a number of factors including, but not limited to, the type and amount of samples and characteristics of samples to be analyzed, the physical space constraint for the optical computing device, and the like.

As shown in FIG. 3, the electromagnetic radiation sources 302a,b,c may be located at a unique angular displacement relative to the optical train. The angular displacement about the optical train may be at a location before or after the rotatable BASF 304, without departing from the scope of the present disclosure. Moreover, some of the electromagnetic radiation sources may be located before the rotatable BASF described herein, and others may be located after the rotatable BASF in a particular optical computing device, or all of the electromagnetic radiation sources may be before or after the rotatable BASF in a particular optical computing device, without departing from the scope of the present disclosure. The unique angular displacement of each electromagnetic radiation source 302a,b,c permits optical interaction of the emitted electromagnetic radiation 312a,b,c with the rotatable BASF at a particular and unique angle of incidence.

In practice, each of the electromagnetic radiation sources 302a,b,c may be used independently. That is, only one of the electromagnetic radiation sources 302a,b,c emits electromagnetic radiation 312a,b,c, respectively, at any particular time into the optical train to impinge upon the rotatable BASF, sample, and ICE, in any order. In such a way, the particular wavelength or band of wavelengths desired for optical interaction with a particular sample or characteristic of a sample may be selectively chosen by rotating the rotatable BASF 304 to collect the electromagnetic radiation from the desired electromagnetic radiation source based on the target angle of incidence.

As shown in FIG. 3, the electromagnetic radiation sources 302a,b,c are displaced at a unique angular location about the optical train to emit electromagnetic radiation 312a,b,c into the optical train. The electromagnetic radiation 312a,b,c may then encounter the rotatable BASF 304 of the present disclosure. The rotatable BASF 304 may be composed of a BASF as described previously, where the BASF is rotatable about an axis that is perpendicular to the optical train. The rotatable BASF 304 may be rotatable by any means that does not interfere with the ability of the BASF to transmit or reflect electromagnetic radiation at particular angles of incidence, as described herein. For example, the rotatable BASF 304 may be rotatable by a rod or clamp mechanism located at a point or along the perimeter of the BASF, such as at a location that does not encounter electromagnetic radiation, or at a location in which electromagnetic radiation need not be transmitted or reflected. In some instances, the rod or clamp may be located at the top or bottom of the rotatable BASF 304, and may or may not span the entire width of the perimeter of the BASF. Other fastening mechanisms to allow the rotatable BASF 304 to rotate about an axis perpendicular to the optical train may also be used, such as by means of mechanical fasteners, brazing or welding techniques, adhesives, magnets, other fastening devices, combinations thereof, or the like.

The rotation of the rotatable BASF 304 may be achieved by any means capable of positioning the rotatable BASF 304 at an angular orientation that is capable of receiving electromagnetic radiation 312a,b,c from particular electromagnetic radiation source 302,a,b,c based on angle of incidence. In some embodiments, the rotation of the rotatable BASF 304 may be achieved by mechanical rotation (e.g., manual rotation), electrical rotation (e.g., computer controlled), and any combination thereof. That is, in some instances, the same rotatable BASF 304 may be capable of both electrical rotation and mechanical rotation (e.g., the electrical rotation may be overridden). Rotation may be achieved by a screw, a crank, a rod, a computer controlled connection, and the like, and combinations thereof. Other means of rotation may also be employed in the embodiments described herein, without departing from the scope of the present disclosure.

Angle selection of the rotatable BASF 304 is based on which electromagnetic radiation source 302a,b,c is to be interacted with the sample 306. Once rotated, the angle of incidence of the selected electromagnetic radiation source 302a,b,c is transmitted through the rotatable BASF 304 into the optical train, due to its angular orientation. For example, when the rotatable BASF 304 is rotated at Brewster's angle ("θB"), electromagnetic source 302a is fully transmitted by the rotatable BASF 304 into the optical train. When the rotatable BASF 304 is rotated more than θB, electromagnetic radiation 312b from electromagnetic radiation source 302b is fully transmitted by the rotatable BASF 304 into the optical train. Finally, when the rotatable BASF 304 is rotated less than the θB, electromagnetic radiation 312c from electromagnetic radiation source 302c is fully transmitted by the rotatable BASF 304 into the optical train. Additionally, at these angles, the rotatable BASF 304 reflects radiation signals that are not coincident with the target angle of incidence. For example, as shown in FIG. 3, the rotatable BASF 304 may be rotated to transmit the electromagnetic radiation 312a at a target angle of incidence from source 302a, and reflect one or more stray light radiation signals 314 that are not coincident with the target angle of incidence. This permits each of the electromagnetic radiation sources 302a,b,c to be in operation (e.g., illuminated) simultaneously, but allow transmission of only one selected electromagnetic radiation source 302a,b,c at any one time. Although not shown, when the rotatable BASF 304 is rotated to accept electromagnetic radiation 312b,c, similar stray light reflections that are not coincident with the target angle of incidence from the selected electromagnetic radiation source 302a,b,c may also be reflected by the rotatable BASF 304.

Although the rotatable BASF 304 in FIG. 3 is located at a position to receive the electromagnetic radiation 312a,b,c directly from one of the electromagnetic radiation sources 302a,b,c, it will be appreciated that the rotatable BASF 304 may be located at any point along the optical train before the ICE 308, without departing from the scope of the present disclosure. For example, the rotatable BASF 304 may be located between the sample 306 and the ICE 308, where the sample 306 is itself located either before, without departing from the scope of the present disclosure. That is, the rotatable BASF 304 is capable of distinguishing signals corresponding to a particular electromagnetic radiation source 302a,b,c based on a target angle of incidence regardless of its location in the optical train.

In some embodiments, the rotatable BASF of the present disclosure may be a stand-alone filter, as shown in FIG. 3 (and FIG. 4 below). As used herein, the term "stand-alone filter," and grammatical variants thereof, refers to a rotatable broadband angle-selective filter as described herein that is not integral to any component of the optical computing devices described herein. When the BASF is a stand-alone filter, as described previously, it may be located at any location in the optical train including, but not limited to, between the electromagnetic radiation source and the sample, between the sample and the ICE, between the ICE and the detector, and any combination thereof. It may then optically interact with one or more of the electromagnetic radiation, the optically interacted radiation, the modified electromagnetic radiation, and any combination thereof. As used herein, the term "optically interacted radiation" refers to electromagnetic radiation that has optically interacted radiation with either a sample or an ICE, but not both. As used herein, the term "modified electromagnetic radiation" refers to electromagnetic radiation that has optically interacted with both a sample and an ICE in any order.

In other embodiments (not shown), the rotatable BASF may be in the form of a multi-layer film stack that is deposited onto a component of the optical computing devices described herein. Such multi-layer film stack rotatable BASFs may be deposited onto a component including, but not limited to, the ICE in the optical computing devices described herein. In other embodiments, the multi-layer film stack rotatable BASFs may be deposited onto a sampling window, where included in the optical computing device as discussed below, without departing from the scope of the present disclosure. In such embodiments, the component itself may be rotatable to accommodate the rotation of the rotatable BASF in the same manner, or by the same means, discussed previously with reference to FIG. 3 to rotate the rotatable BASF to an angle to accept a target angle of incidence of electromagnetic radiation, optically interacted electromagnetic radiation, and/or modified electromagnetic radiation. Moreover, any other means may be employed for rotating the rotatable BASF when it is in the form of a deposited multi-layer film stack on a component of the optical computing devices described herein, without departing from the scope of the present disclosure.

Standard thin film deposition methods may be utilized for depositing the multi-stack film layer onto one or more components of the optical computing devices described herein, without departing from the scope of the present disclosure. In some embodiments, the deposition may be achieved by fabricating the rotatable BASF from an optical substrate, which then may operate as an ICE. In other embodiments, the multi-layer film stack may be deposited onto one or more components of the optical computing devices using reactive magnetron sputtering, electron-beam thermal evaporation, chemical vapor deposition, and the like, and any combination thereof.

As shown in FIG. 3, after transmitting the desired electromagnetic radiation 312a,b,c from the desired electromagnetic radiation source 302a,b,c through the rotated rotatable BASF 304, the electromagnetic radiation 312a,b,c optically interacts with the sample 306. As a result, the electromagnetic radiation 312a,b,c reflects from the sample, generating optically interacted radiation (e.g., sample-interacted light) 316a,b,c. Those skilled in the art, however, will readily recognize that alternative variations of the device 300 may allow the optically interacted radiation 316a,b,c to be generated by being transmitted, scattered, diffracted, absorbed, emitted, or re-radiated by and/or from the sample 306, or one or more analytes of the sample 306, without departing from the scope of the present disclosure.

As previously mentioned, in some embodiments, the sample may be located in a flow path, static, moving on a conveyor belt, and the like. In some embodiments, the flow path may be located in a wellbore in a subterranean formation, and the sample may be flowing. In other embodiments, the static sample may also be located in a subterranean formation, such as from a sample taken by a formation tester, or otherwise located outside of a subterranean formation or therein in a holding vessel. In some embodiments, a sampling window may be in the optical train located adjacent to or otherwise in contact with the sample 306 (e.g., it may form a portion of the flow path, for example), where the electromagnetic radiation 312a,b,c passes through the sampling window prior to impinging on the sample 306 to generate the optically interacted radiation 316a,b,c. The sampling window may be composed from a variety of transparent, rigid or semi-rigid materials that are configured to allow transmission of the electromagnetic radiation 312a, b,c therethrough (or any other radiation signal in the optical train, as described below). For example, the sampling window may be made composed of, but is not limited to, glasses, plastics, semi-conductors, crystalline materials, polycrystalline materials, hot or cold-pressed powders, combinations thereof, or the like. In some embodiments, the sampling window may serve a dual purpose as both a transmission window and an ICE (i.e., a spectral component).

The optically interacted radiation 316a,b,c generated by the interaction with the sample 306 may be directed to or otherwise received by an ICE 308 arranged in the optical train. The ICE 308 may be a spectral component substantially similar to the ICE 100 described above with reference to FIG. 1. Accordingly, in operation the ICE 308 may be configured to receive the optically interacted radiation 316a, b,c and produce modified electromagnetic radiation 318a,b,c corresponding to a particular characteristic of interest of the sample 306.

As previously stated, the term "optically interacted radiation" refers to electromagnetic radiation that has optically interacted radiation with either a sample or an ICE, but not both, and the term "modified electromagnetic radiation" refers to electromagnetic radiation that has optically interacted with both a sample and an ICE in any order. For example, as shown in FIG. 3, and discussed previously, in some embodiments the ICE 308 is located in the optical train after the sample 306, wherein the electromagnetic radiation 312a,b,c first optically interacts with the sample 306 to generate optically interacted radiation 316a,b,c (e.g., sample-interacted light), and then the optically interacted radiation 316a,b,c optically interacts with the ICE 308 to generate the modified electromagnetic radiation 318a,b,c in the optical train. In other embodiments, the ICE 308a (shown in phantom) may be located before the sample 306 in an optical train, wherein electromagnetic radiation 312a, b,c first optically interacts with the ICE 308 to generate optically interacted radiation 316a,b,c in an optical train, and then the optically interacted radiation 316a,b,c optically interacts with the sample 306 to generate the modified electromagnetic radiation 318a,b,c in the optical train. That is, the order of the sample 306 relative to the ICE 308, 308a in the optical train is not limiting and does not interfere with the ability of the optical computing device 300 to detect a characteristic of interest of the sample 306.

While only one ICE 308 is shown in the device 300, embodiments are contemplated herein which include the use of at least two ICE components in the device 308 configured to cooperatively determine the characteristic of interest in the sample 306. For example, two or more ICE 308 components may be arranged in series or parallel within the device 300 at any point along the optical train and configured to receive the electromagnetic radiation 312a,b,c, the optically interacted radiation 316a,b,c, and/or the modified electromagnetic radiation 318a,b,c, without departing from the scope of the present disclosure. The two or more ICE 308 components may be used to enhance sensitivities and detector limits of the device 300.

Although not shown in FIG. 3, it will be appreciated that one or more non-rotatable BASFs may be located at any point along the optical train after the rotatable BASF 304, including before or after the sample 306, without departing from the scope of the present disclosure. The non-rotatable BASFs may serve to further ensure that only electromagnetic radiation 312a,b,c, optically interacted electromagnetic radiation 316a,b,c, and modified electromagnetic radiation 318a,b,c at a particular target angle of incidence or range thereof remains in the optical train at any particular point. Each of the additional non-rotatable BASFs, where included in the optical train, may be tuned to transmit the same angle of incidence or different angles of incidence depending on their location in the optical train, the electromagnetic radiation expected to be optically interacted with the BASFs, and the like.

Electromagnetic radiation that has optically interacted with at least one of the rotatable BASF 304, the sample 306, and the ICE 308 may be term herein "angle-selected modified electromagnetic radiation" ("ASMR") (not shown). It is the ASMR that may be received by a detector 310 for analysis and quantification. Moreover, the detector 310 may receive a plurality of ASMR signals from a plurality of unique orientations of the rotatable BASF 304 in the device 300, without departing from the scope of the present disclosure. That is, the detector 310 may receive more than one signal originating from more than one electromagnetic radiation source 302a,b,c. The detector 310 may be any device capable of detecting electromagnetic radiation, and may be generally characterized as an optical transducer. In some embodiments, the detector 310 may be, but is not limited to, a thermal detector such as a thermopile or photoacoustic detector, a semiconductor detector, a piezo-electric detector, a charge coupled device (CCD) detector, a video or array detector, a split detector, a quad detector, a photon detector (such as a photomultiplier tube), photodiodes, combinations thereof, and the like, or other detectors known to those skilled in the art.

In some embodiments, the detector 310 may be configured to produce an output signal 426 in real-time or near real-time in the form of a voltage (or current) that corresponds to the particular characteristic of interest of the sample 306. The voltage returned by the detector 310 is essentially the dot product of the optical interaction of the ASMR with respect to the ICE 308 as a function of the characteristic of interest. As such, the output signal produced by the detector 310 and the characteristic of interest may have a relationship that is directly proportional or may correspond to a polynomial function, an exponential function, a logarithmic function, a combination thereof, or the like.

In some embodiments, the reflected stray signal(s) from the rotatable BASF 304 that are not coincident with the target angle of incidence, for example stray signal 314, may be related to certain characteristics of the sample 306 or may simply be non-sample 306 related light, and may be directed away from the detector 318. In alternative configurations (not shown), a second ICE may be positioned such that the reflected stray signal(s) 314 optically interact therewith to be conveyed to a second detector substantially similar, if not the same, as the detector 310, without departing from the scope of the present disclosure.

The characteristic(s) of interest being analyzed using the optical computing device 300 may be further processed and/or analyzed computationally to provide additional characterization information about the sample 306, or an analyte thereof. In some embodiments, the identification and concentration of one or more analytes of a sample 306 may be used to predict certain physical characteristics of the sample 306, or analyte thereof. For example, the amount of the sample 306 may be evaluated to determine, for example, whether it is present within acceptable limits. Accordingly, where one or more optical computing devices 300 is used according to the methods herein to detect a characteristic of interest of a sample 306, different acceptable limit ranges may apply to the one or more characteristics.

In some embodiments, the magnitude of the characteristic of interest determined using the optical computing device 300 may be fed into an algorithm operating under computer control. The algorithm may be configured to determine whether the sample 306 or characteristic of interest of the sample 306 is within acceptable limits, which may be narrowed or broadened depending on a particular operation. In some embodiments, the algorithm may produce an output that is readable by an operator who can manually take appropriate action, if needed, based upon the reported output. In some embodiments, the algorithm may direct the operator as to how to take a corrective action (e.g., how to bring the amount of the sample 306 or characteristic of interest of the sample 306 within acceptable limits). In other embodiments, the algorithm may take proactive process control (e.g., halt operations, alter a composition comprising the sample 306 or characteristic of interest of the sample 306, and the like). It is to be recognized that the algorithm (e.g., an artificial neural network) may be trained using samples of predetermined characteristics of interest, and thereby generating a virtual library. As the virtual library available to the artificial neural network becomes larger, the neural network may become more capable of accurately predicting the sample 306 or characteristic of interest of the sample 306. Furthermore, with sufficient training, the artificial neural network may more accurately predict the sample 306 or characteristic of interest of the sample 306, even in the presence of unknown analytes.

In some embodiments, the data collected using the optical computing devices 300 may be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system may also allow remote monitoring to take place. Automated control with a long-range communication system may further facilitate the performance of remote job operations. In particular, an artificial neural network may be used in some embodiments to facilitate the performance of remote job operations. That is, remote job operations may be conducted automatically in some embodiments. In other embodiments, however, remote job operations may occur under direct operator control, where the operator is not at the job site (e.g., via wireless technology).

In some applications, the output signal of the detector 310 (or any additional detectors used) may be conveyed to or otherwise received by a signal processor communicably coupled to the detector 310. The signal processor may be a computer including a non-transitory machine-readable medium. For example, the concentration or magnitude of each characteristic of interest determined using the optical computing device 300 may be fed into an algorithm run by the signal processor.

In real-time or near real-time, the signal processor 434 may be configured to provide a processed output signal corresponding to a characteristic of interest in the sample 306. The resulting processed output signal may be readable by an operator who can consider the results and make proper adjustments or take appropriate action, if needed, based upon output signal related to the sample 306 (e.g., a concentration of the sample 306 or a concentration of a characteristic of the sample 306). In some embodiments, the resulting processed signal output may be conveyed, either wired or wirelessly, to an operator for consideration. In other embodiments, the resulting processed output signal of the characteristic of interest may be recognized by the signal processor as being within or without an acceptable limit range for a particular operation and may alert the operator of an out of range reading so appropriate corrective action may be taken, or otherwise autonomously undertake the appropriate corrective action such that the resulting processed output signal returns to a value within the predetermined or preprogrammed range of suitable operation.

Figure 4:
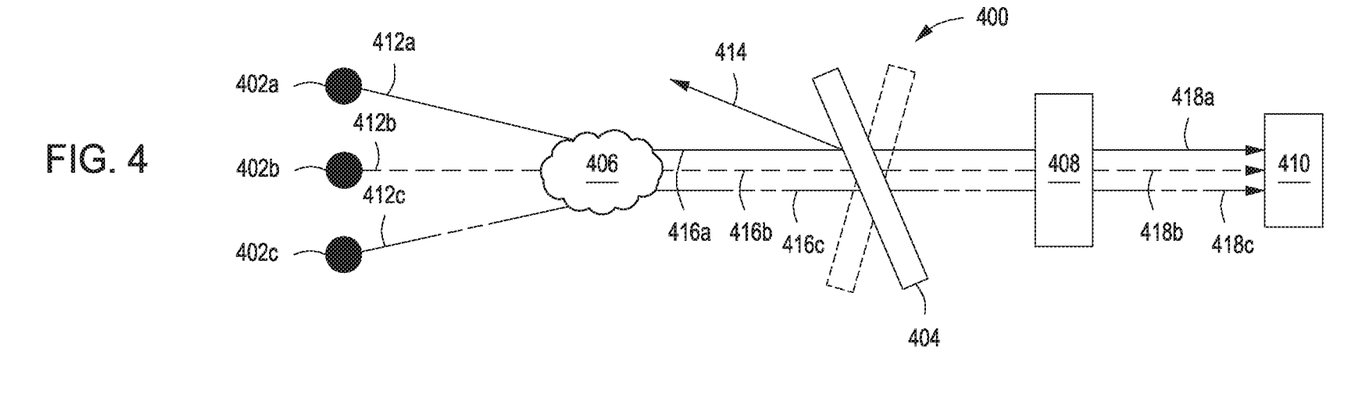
FIG. 4 illustrates an optical computing device comprising a rotatable broadband angle-selective filter, according to one or more embodiments described herein.

Referring now to FIG. 4, illustrated is another embodiment of an optical computing device 400 employing the rotatable BASFs of the present disclosure. The optical computing device 400 is substantially similar to the optical computing device 300 of FIG. 3. Accordingly, like components will not be discussed again in detail. Electromagnetic radiation sources 402*a,b,c* are each displaced at a unique angular location about the optical train and each have a unique wavelength (e.g., single, narrow, or broadband wavelengths). The electromagnetic radiation 412*a,b,c* first impinges on the sample 406 to generate optically interacted radiation 416*a,b,c*. The optically interacted radiation 416*a,b,c* may thereafter encounter a rotatable BASF 404 that is rotatable to transmit the optically interacted radiation 416*a,b,c* that originated from one of the electromagnetic radiation sources 402*a,b,c* based on a target angle of incidence. The rotatable BASF may also, as previously described, reflect stray radiation signals that are not coincident with the target angle of incidence, such as stray signal 414 from electromagnetic radiation source 402*a*.

After transmission through the rotatable BASF 404, the optically interacted radiation that has optically interacted with the sample 406 and the rotatable BASF 404 may be directed to or otherwise received by an ICE 408 arranged in the optical train to produce modified electromagnetic radiation 418*a,b,c* corresponding to a particular characteristic of interest of the sample 406. In particular, the modified electromagnetic radiation 418*a,b,c* may approximately mimic the regression vector corresponding to the characteristic of interest. After optically interacting with at least one of the sample 406, the rotatable BASF 404, and the ICE 408, generating ASMR, the ASMR may be received by a detector 410 for analysis and quantification.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM, and flash EPROM.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Embodiments herein include:

Embodiment A

An optical computing device comprising: a plurality of electromagnetic radiation sources, each at a unique angular displacement about an optical train and each at at least one unique electromagnetic radiation wavelength; an integrated computational element (ICE) located in the optical train before or after a sample located in the optical train to generate modified electromagnetic radiation in the optical train; a broadband angle-selective filter (BASF) located in the optical train that is rotatable about an axis to a plurality of unique orientations to transmit the electromagnetic radiation and/or the modified electromagnetic radiation in the optical train at a target incident angle corresponding to one of the plurality of electromagnetic radiation sources to generate angle selected-modified electromagnetic radiation (ASMR); and a detector to receive the ASMR and to generate an output signal corresponding to a characteristic of the sample.

Embodiment A may have one or more of the following additional elements in any combination:

Element A1: Wherein the ICE is located after the sample so that the electromagnetic radiation first optically interacts with the sample to generate optically interacted radiation in the optical train, and then the optically interacted radiation optically interacts with the ICE to generate the modified electromagnetic radiation in the optical train, and wherein the BASF is located in the optical train to transit the electromagnetic radiation, the optically interacted radiation, and/or the modified electromagnetic radiation in the optical train at the target incident angle.

Element A2: Wherein the ICE is located before the sample so that the electromagnetic radiation first optically interacts with the ICE to generate optically interacted radiation in the optical train, and then the optically interacted radiation optically interacts with the sample to generate the modified electromagnetic radiation in the optical train, and wherein the BASF is located in the optical train to transit the electromagnetic radiation, the optically interacted radiation, and/or the modified electromagnetic radiation in the optical train at the target incident angle.

Element A3: Wherein the detector is in the optical train to receive a plurality of ASMR from a plurality of unique orientations of the rotatable BASF.

Element A4: Wherein the sample is contained in a flow path to permit optical interaction with the electromagnetic radiation or the optically interacted radiation therewith.

Element A5: Wherein the plurality of electromagnetic radiation sources are selected from the group consisting of narrow band sources, broadband sources, and any combination thereof.

Element A6: Wherein the BASF is a multi-layer film stack deposited on the ICE.

Element A7: Wherein a sample window is arranged adjacent to the sample in the optical train.

Element A8: Wherein a sample window is arranged adjacent to the sample in the optical train, and wherein the BASF is a multi-layer film stack deposited onto a component selected from the group consisting of the ICE, the sampling window, and any combination thereof.

Element A9: Wherein the BASF is composed of photonic crystal layers.

Element A10: Wherein the BASF is composed of photonic crystal layers selected from the group consisting of a silicon-based compound, a tantalum-based compound, a Group III-V semiconductor compound, a Group IVB metal compound, a dielectric, a thin film deposition compound, and any combination thereof.

By way of non-limiting example, exemplary combinations applicable to A include: By way of non-limiting example, exemplary combinations applicable to A include: A with A1 and A2; A with A1 and A3; A with A1 and A4; A with A1 and A5; A with A1 and A6; A with A1 and A7; A with A1 and A8; A with A1 and A9; A with A1 and A10; A with A2 and A3; A with A2 and A4; A with A2 and A5; A with A2 and A6; A with A2 and A7; A with A2 and A8; A with A2 and A9; A with A2 and A10; A with A3 and A4; A with A3 and A5; A with A3 and A6; A with A3 and A7; A with A3 and A8; A with A3 and A9; A with A3 and A10; A with A4 and A5; A with A4 and A6; A with A4 and A7; A with A4 and A8; A with A4 and A9; A with A4 and A10; A with A5 and A6; A with A5 and A7; A with A5 and A8; A with A5 and A9; A with A5 and A10; A with A6 and A7; A with A6 and A8; A with A6 and A9; A with A6 and A10; A with A7 and A8; A with A7 and A9; A with A7 and A10; A with A8 and A9; A with A8 and A10; A with A9 and A10; A with A1, A2, A3, A4, A5, A6, A7, A8, A9, and A10; A with A1, A3, A5, and A8; A with A1, A2, A6, and A7; A with A2, A4, and A8; A with A1, A5, A9, and A10.

Embodiment B

A method comprising: providing a plurality of electromagnetic radiation sources, each at a unique angular displacement about an optical train and each at least one unique electromagnetic radiation wavelength; optically interacting the electromagnetic radiation with a sample located in the optical train and an integrated computational element (ICE) located in the optical train before or after the sample to generate modified electromagnetic radiation in the optical train; transmitting the electromagnetic radiation and/or the modified electromagnetic radiation through a broadband angle-selective filter (BASF) located in the optical train, wherein the BASF is rotatable about an axis to a plurality of unique orientations in the optical train at a target incident angle corresponding to one of the plurality of electromagnetic radiation sources, thereby generating angle selected-modified electromagnetic radiation (ASMR); receiving the AMSR with a detector; and generating an output signal corresponding to a characteristic of the sample.

Embodiment B may have one or more of the following additional elements in any combination:

Element B1: Wherein the ICE is located after the sample so that the electromagnetic radiation first optically interacts with the sample to generate optically interacted radiation in the optical train, and then the optically interacted radiation optically interacts with the ICE to generate the modified electromagnetic radiation in the optical train, and wherein the BASF is located in the optical train to transit the electromagnetic radiation, the optically interacted radiation, and/or the modified electromagnetic radiation in the optical train at the target incident angle.

Element B2: wherein the ICE is located before the sample so that the electromagnetic radiation first optically interacts with the ICE to generate optically interacted radiation in the optical train, and then the optically interacted radiation optically interacts with the sample to generate the modified electromagnetic radiation in the optical train, and wherein the BASF is located in the optical train to transit the electromagnetic radiation, the optically interacted radiation, and/or the modified electromagnetic radiation in the optical train at the target incident angle.

Element B3: Further comprising receiving a plurality of ASMR with the detector from a plurality of unique orientations of the rotatable BASF.

Element B4: Further comprising containing the sample in a flow path that permits optical interaction with the electromagnetic radiation or the optically interacted radiation therewith.

Element B5: Wherein the plurality of electromagnetic radiation sources are selected from the group consisting of narrow band sources, broadband sources, and any combination thereof.

Element B6: Wherein the BASF is a multi-layer film stack deposited on the ICE.

Element B7: Wherein a sample window is arranged adjacent to the sample in the optical train.

Element B8: Wherein a sample window is arranged adjacent to the sample in the optical train, and wherein the BASF is a multi-layer film stack deposited onto a component selected from the group consisting of the ICE, the sampling window, and any combination thereof.

Element B9: Wherein the BASF is composed of photonic crystal layers.

Element B10: Wherein the BASF is composed of photonic crystal layers selected from the group consisting of a silicon-based compound, a tantalum-based compound, a Group III-V semiconductor compound, a Group IVB metal compound, a dielectric, a thin film deposition compound, and any combination thereof.

By way of non-limiting example, exemplary combinations applicable to B include: B with B1 and B2; B with B1 and B3; B with B1 and B4; B with B1 and B5; B with B1 and B6; B with B1 and B7; B with B1 and B8; B with B1 and B9; B with B1 and B10; B with B2 and B3; B with B2 and B4; B with B2 and B5; B with B2 and B6; B with B2 and B7; B with B2 and B8; B with B2 and B9; B with B2 and B10; B with B3 and B4; B with B3 and B5; B with B3 and B6; B with B3 and B7; B with B3 and B8; B with B3 and B9; B with B3 and B10; B with B4 and B5; B with B4 and B6; B with B4 and B7; B with B4 and B8; B with B4 and B9; B with B4 and B10; B with B5 and B6; B with B5 and B7; B with B5 and B8; B with B5 and B9; B with B5 and B10; B with B6 and B7; B with B6 and B8; B with B6 and B9; B with B6 and B10; B with B7 and B8; B with B7 and B9; B with B7 and B10; B with B8 and B9; B with B8 and B10; B with B9 and B10; B with B1, B2, B3, B4, B5, B6, B7, B8, B9, and B10; B with B1, B2, B7, and B8; B with B1, B3, B4, and B6; B with B4, B5, and B7; B with B3, B5, B9, and B10.

Embodiment C

A system comprising: a sample arranged in an optical train; and an optical computing device arranged in the optical train to optically interact with the sample, the optical computing device comprising: a plurality of electromagnetic radiation sources, each at a unique angular displacement about an optical train and each at at least one unique electromagnetic radiation wavelength; an integrated computational element (ICE) located in the optical train before or after a sample located in the optical train to generate modified electromagnetic radiation in the optical train; a broadband angle-selective filter (BASF) located in the optical train that is rotatable about an axis to a plurality of unique orientations to transmit the electromagnetic radiation and/or the modified electromagnetic radiation in the optical train at a target incident angle corresponding to one of the plurality of electromagnetic radiation sources to generate angle selected-modified electromagnetic radiation (ASMR); and a detector to receive the ASMR and to generate an output signal corresponding to a characteristic of the sample.

Embodiment C may have one or more of the following additional elements in any combination:

Element C1: Wherein the ICE is located after the sample so that the electromagnetic radiation first optically interacts with the sample to generate optically interacted radiation in the optical train, and then the optically interacted radiation optically interacts with the ICE to generate the modified electromagnetic radiation in the optical train, and wherein the BASF is located in the optical train to transit the electromagnetic radiation, the optically interacted radiation, and/or the modified electromagnetic radiation in the optical train at the target incident angle.

Element C2: Wherein the ICE is located before the sample so that the electromagnetic radiation first optically interacts with the ICE to generate optically interacted radiation in the optical train, and then the optically interacted radiation optically interacts with the sample to generate the modified electromagnetic radiation in the optical train, and wherein the BASF is located in the optical train to transit the electromagnetic radiation, the optically interacted radiation, and/or the modified electromagnetic radiation in the optical train at the target incident angle.

Element C3: Wherein sample is in a flow path.

Element C4: Wherein sample is in a flow path, and wherein the flow path is located in a wellbore in a subterranean formation.

Element C5: Wherein the detector is in the optical train to receive a plurality of ASMR from a plurality of unique orientations of the rotatable BASF.

Element C6: Wherein the plurality of electromagnetic radiation sources are selected from the group consisting of narrow band sources, broadband sources, and any combination thereof.

Element C7: Wherein the BASF is a multi-layer film stack deposited on the ICE.

Element C8: Wherein a sample window is arranged adjacent to the sample in the optical train.

Element C9: Wherein a sample window is arranged adjacent to the sample in the optical train, and wherein the BASF is a multi-layer film stack deposited onto a component selected from the group consisting of the ICE, the sampling window, and any combination thereof.

Element C10: Wherein the BASF is composed of photonic crystal layers.

Element C11: Wherein the BASF is composed of photonic crystal layers selected from the group consisting of a silicon-based compound, a tantalum-based compound, a Group III-V semiconductor compound, a Group IVB metal compound, a dielectric, a thin film deposition compound, and any combination thereof.

By way of non-limiting example, exemplary combinations applicable to C include: C with C1 and C2; C with C1 and C3; C with C1 and C4; C with C1 and C5; C with C1 and C6; C with C1 and C7; C with C1 and C8; C with C1 and C9; C with C1 and C10; C with C1 and C11; C with C2 and C3; C with C2 and C4; C with C2 and C5; C with C2 and C6; C with C2 and C7; C with C2 and C8; C with C2 and C9; C with C2 and C10; C with C2 and C11; C with C3 and C4; C with C3 and C5; C with C3 and C6; C with C3 and C7; C with C3 and C8; C with C3 and C9; C with C3 and C10; C with C3 and C11; C with C4 and C5; C with C4 and C6; C with C4 and C7; C with C4 and C8; C with C4 and C9; C with C4 and C10; C with C4 and C11; C with C5 and C6; C with C5 and C7; C with C5 and C8; C with C5 and C9; C with C5 and C10; C with C5 and C11; C with C6 and C7; C with C6 and C8; C with C6 and C9; C with C6 and C10; C with C6 and C11; C with C7 and C8; C with C7 and C9; C with C7 and C10; C with C7 and C11; C with C8 and C9; C with C8 and C10; C with C8 and C11; C with C9 and C10; C with C9 and C11; C with C10 and C11; C with C1, C2, C3, C4, C5, C6, C7, C8, C9, C10, and C11; C with C1, C3, C7, and C8; C with C1, C4, C6, and C9; C with C5, C7, and C8; C with C1, C4, and C9; C with C2, C6, and C7; C with C5, C6, C10, and C11.

Therefore, the exemplary embodiments described herein are well adapted to attain the ends and advantages mentioned as well as those that are inherent therein. The particular embodiments disclosed above are illustrative only, as the exemplary embodiments described herein may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The invention claimed is:

1. An optical computing device comprising:
   a plurality of electromagnetic radiation sources, each at a unique angular displacement about an optical train and each at at least one unique electromagnetic radiation wavelength;
   an integrated computational element (ICE) located in the optical train before or after a sample located in the optical train to generate modified electromagnetic radiation in the optical train;
   a broadband angle-selective filter (BASF) located in the optical train that is rotatable about an axis to a plurality of unique orientations to transmit the electromagnetic radiation and/or the modified electromagnetic radiation in the optical train at a target incident angle corresponding to one of the plurality of electromagnetic radiation sources to generate angle selected-modified electromagnetic radiation (ASMR); and
   a detector to receive the ASMR and to generate an output signal corresponding to a characteristic of the sample.

2. The optical computing device of claim 1, wherein the ICE is located either (A) after the sample so that the electromagnetic radiation first optically interacts with the sample to generate optically interacted radiation in the optical train, and then the optically interacted radiation optically interacts with the ICE to generate the modified electromagnetic radiation in the optical train, or (B) before the sample so that the electromagnetic radiation first optically interacts with the ICE to generate optically interacted radiation in the optical train, and then the optically interacted radiation optically interacts with the sample to generate the modified electromagnetic radiation in the optical train, and
   wherein the BASF is located in the optical train to transit the electromagnetic radiation, the optically interacted radiation, and/or the modified electromagnetic radiation in the optical train at the target incident angle.

3. The optical computing device of claim 2, wherein the detector is in the optical train to receive a plurality of ASMR from a plurality of unique orientations of the rotatable BASF.

4. The optical computing device of claim 2, wherein the sample is contained in a flow path to permit optical interaction with the electromagnetic radiation or the optically interacted radiation therewith.

5. The optical computing device of claim 2, wherein the plurality of electromagnetic radiation sources are selected from the group consisting of narrow band sources, broadband sources, and any combination thereof.

6. The optical computing device of claim 2, wherein the BASF is a multi-layer film stack deposited on the ICE.

7. The optical computing device of claim 2, wherein a sample window is arranged adjacent to the sample in the optical train.

8. The optical computing device of claim 7, wherein the BASF is a multi-layer film stack deposited onto a component selected from the group consisting of the ICE, the sampling window, and any combination thereof.

9. The optical computing device of claim 2, wherein the BASF is composed of photonic crystal layers.

10. The optical computing device of claim 9, wherein the photonic crystal layers are selected from the group consisting of a silicon-based compound, a tantalum-based compound, a Group III-V semiconductor compound, a Group IVB metal compound, a dielectric, a thin film deposition compound, and any combination thereof.

11. A method comprising:
    providing a plurality of electromagnetic radiation sources, each at a unique angular displacement about an optical train and each at least one unique electromagnetic radiation wavelength;
    optically interacting the electromagnetic radiation with a sample located in the optical train and an integrated computational element (ICE) located in the optical train before or after the sample to generate modified electromagnetic radiation in the optical train;
    transmitting the electromagnetic radiation and/or the modified electromagnetic radiation through a broadband angle-selective filter (BASF) located in the optical train, wherein the BASF is rotatable about an axis to a plurality of unique orientations in the optical train at a target incident angle corresponding to one of the plurality of electromagnetic radiation sources, thereby generating angle selected-modified electromagnetic radiation (ASMR);
    receiving the ASMR with a detector; and
    generating an output signal corresponding to a characteristic of the sample.

12. The method of claim 11, wherein the ICE is located either (A) after the sample so that the electromagnetic radiation first optically interacts with the sample to generate optically interacted radiation in the optical train, and then the optically interacted radiation optically interacts with the ICE to generate the modified electromagnetic radiation in the optical train, or (B) before the sample so that the electromagnetic radiation first optically interacts with the ICE to generate optically interacted radiation in the optical train, and then the optically interacted radiation optically interacts with the sample to generate the modified electromagnetic radiation in the optical train, and
    wherein the BASF is located in the optical train to transit the electromagnetic radiation, the optically interacted radiation, and/or the modified electromagnetic radiation in the optical train at the target incident angle.

13. The method of claim 12, further comprising receiving a plurality of ASMR with the detector from a plurality of unique orientations of the rotatable BASF.

14. The method of claim 12, further comprising containing the sample in a flow path that permits optical interaction with the electromagnetic radiation or the optically interacted radiation therewith.

15. The method of claim 12, wherein the plurality of electromagnetic radiation sources are selected from the group consisting of narrow band sources, broadband sources, and any combination thereof.

16. The method of claim 12, wherein the BASF is a multi-layer film stack deposited on the ICE.

17. The method of claim 12, wherein a sample window is arranged adjacent to the sample in the optical train.

18. The method of claim 17, wherein the BASF is a multi-layer film stack deposited onto a component selected from the group consisting of the ICE, the sampling window, and any combination thereof.

19. The method of claim 12, wherein the BASF is composed of photonic crystal layers.

20. A system comprising:
    a sample arranged in an optical train; and
    an optical computing device arranged in the optical train to optically interact with the sample, the optical computing device comprising:

a plurality of electromagnetic radiation sources, each at a unique angular displacement about an optical train and each at at least one unique electromagnetic radiation wavelength;

an integrated computational element (ICE) located in the optical train before or after a sample located in the optical train to generate modified electromagnetic radiation in the optical train;

a broadband angle-selective filter (BASF) located in the optical train that is rotatable about an axis to a plurality of unique orientations to transmit the electromagnetic radiation and/or the modified electromagnetic radiation in the optical train at a target incident angle corresponding to one of the plurality of electromagnetic radiation sources to generate angle selected-modified electromagnetic radiation (ASMR); and a detector to receive the ASMR and to generate an output signal corresponding to a characteristic of the sample.

21. The system of claim 20, wherein the ICE is located either (A) after the sample so that the electromagnetic radiation first optically interacts with the sample to generate optically interacted radiation in the optical train, and then the optically interacted radiation optically interacts with the ICE to generate the modified electromagnetic radiation in the optical train, or (B) before the sample so that the electromagnetic radiation first optically interacts with the ICE to generate optically interacted radiation in the optical train, and then the optically interacted radiation optically interacts with the sample to generate the modified electromagnetic radiation in the optical train, and wherein the BASF is located in the optical train to transit the electromagnetic radiation, the optically interacted radiation, and/or the modified electromagnetic radiation in the optical train at the target incident angle.

22. The system of claim 21, wherein sample is in a flow path.

23. The system of claim 22, wherein the flow path is located in a wellbore in a subterranean formation.

* * * * *